US00PP13822P29

(12) United States Plant Patent
Yokoi

(10) Patent No.: US PP13,822 P2
(45) Date of Patent: May 20, 2003

(54) ***ALBIZIA JULIBRISSIN* TREE NAMED 'SUMMER CHOCOLATE'**

(75) Inventor: Masato Yokoi, Kawaguchi (JP)

(73) Assignee: Hines Nurseries, Inc., Irvine, CA (US)

( * ) Notice: Subject to any disclaimer, the term of this patent is extended or adjusted under 35 U.S.C. 154(b) by 0 days.

(21) Appl. No.: 09/662,276

(22) Filed: Sep. 14, 2000

(51) Int. Cl.[7] ..... A01H 5/00
(52) U.S. Cl. ..... Plt./216
(58) Field of Search ..... Plt./216

*Primary Examiner*—Bruce R. Campell
*Assistant Examiner*—Susan B. McCormick
(74) *Attorney, Agent, or Firm*—Christie, Parker & Hale, LLP

(57) ABSTRACT

A new plant variety of *Albizia julibrissin* having burgundy colored foliage and pink and white flowers.

2 Drawing Sheets

BACKGROUND OF THE INVENTION

The present invention relates to a new and distinct variety of *Albizia julibrissin,* which was discovered in 1990 as a seedling in a controlled planting of *Albizia julibrissin* at 337 Akashiba Shinden, Kawaguchi City, Saitama Prefecture, 333 Japan by Dr. Masato Yokoi. The varietal denomination of the new variety is 'Summer Chocolate'.

The genus Albizia is included in the family Leguminosae (alternately Fabaceae or Mimosoideae) which comprises about 150 deciduous tree and shrub genera growing in the northern and southern hemispheres. Albizia Durazz. comprises 7 species of deciduous shrubs, many of which possess desirable ornamental characteristics.

*Albizia julibrissin* is found from Iran to Japan with naturalization occurring in the United States. It generally has alternate, bipinnately compound leaves, up to 50 cm long, with 10–25 pinnae, each with 40–60 leaflets. Leaflets are falcate, oblong, oblique, 0.5–1 mm long, green ciliate and occasionally pubescent on the underside leaflet midrib.

Flowers of *Albizia julibrissin* are borne light to deep pink, fragrant borne in corybose racemes in the summer. Flower colors are lime green to pink.

SUMMARY OF THE INVENTION

The new variety was discovered as a seedling in a controlled planting of *Albizia julibrissin* and differs from its parent in having burgundy colored foliage and dark pink to burgundy colored flowers. Asexual reproduction of the new variety performed in Kawaguchi City , Japan; Lewisberry, Pa.; Vacaville, Calif. and Irvine, Calif. have confirmed that the distinctive characteristics of the new variety are stable and transmitted to succeeding generations.

BRIEF DESCRIPTION OF THE ILLUSTRATIONS

The accompanying illustrations show specimens of the new cultivar in a photo illustration as true to color as is reasonably possible to make in an illustration of this character.

Figure 1:
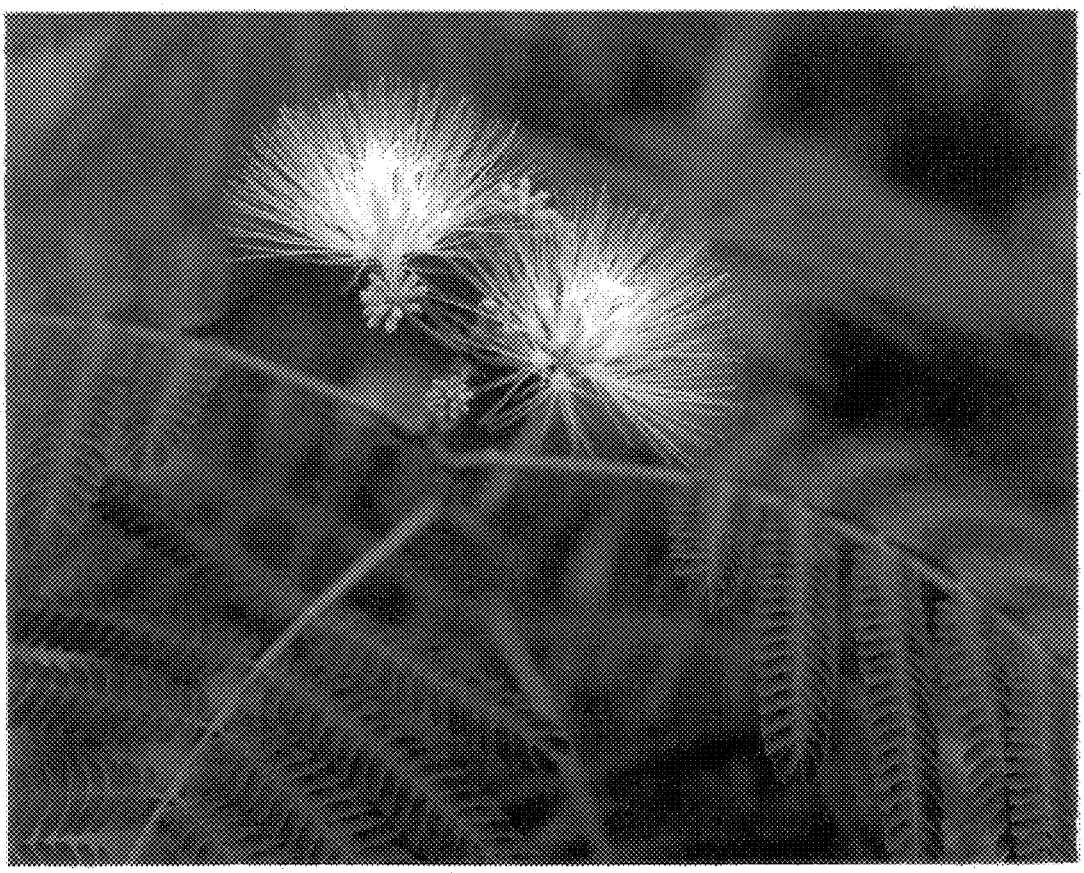

In the illustrations:

FIG. 1 shows the foliage and flower of *Albizia julibissin* 'Summer Chocolate'. Note the distintive burgundy colored flower and foliage.

Figure 2:
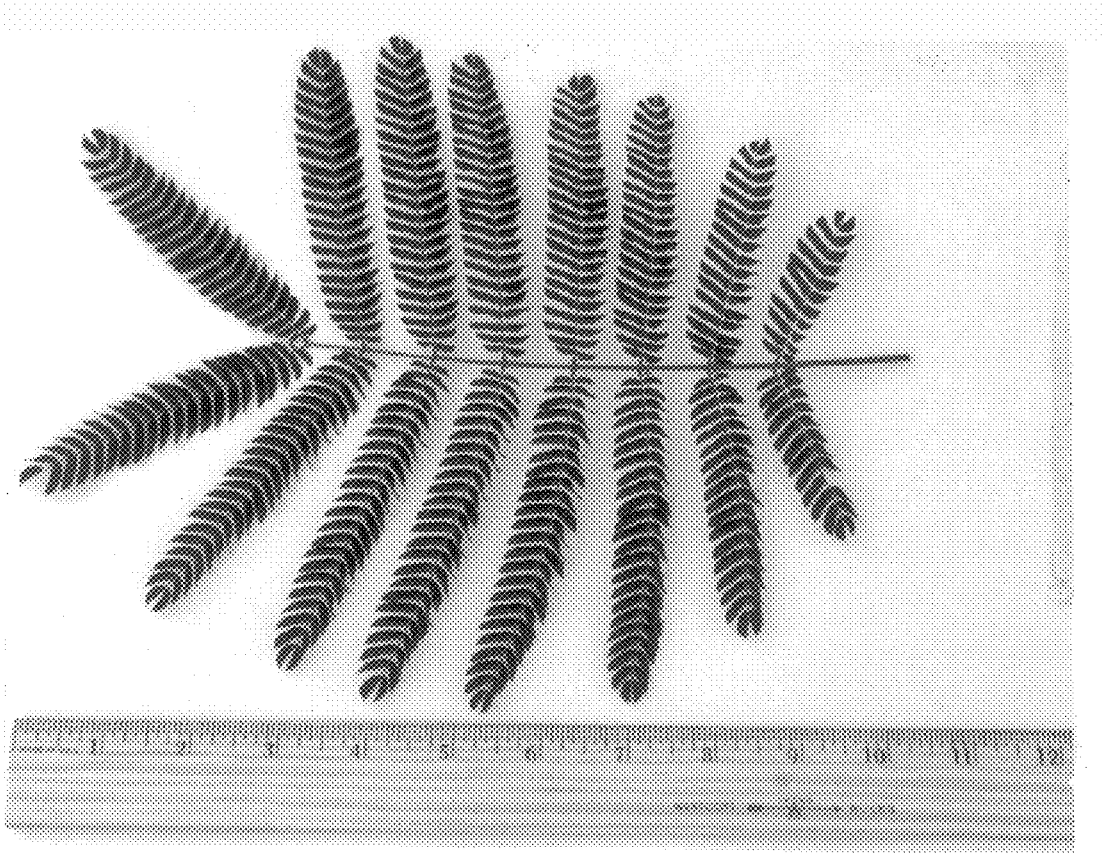

FIG. 2 displays the foliage of the new variety and shows the distinctive burgundy colored foliage.

COMPARISON WITH THE PARENT

The new variety differs from its parent and all other cultivars of *Albizia julibrissin* in having mature foliage which is deep burgundy in color, in contrast to the green leaves and white to pink colored flowers of the foliage of the parent plant and other known cultivars; also, the new variety exhibits a bright pink and white inflorescence in contrast to the typical white to pink inflorescence of the parent and other known cultivars.

DETAILED CESCRIPTION OF THE NEW VARIETY

'SUMMER CHOCOLATE' has not been observed under all possible environmental, cultural, and light conditions. The following observations and descriptions are of 4-year-old plants grown in containers at Lewisberry, Pa.; Irvine, Calif., and Vacaville, Calif.; grown in full sun in production nurseries with overhead irrigation. In this description, color references are to The Royal Horticultural Society Colour Chart 1995 and terminology used in the color descriptions herein refers to plate numbers in this color chart. Phenotypic expression may vary with light intensity, cultural, and environmental conditions.

CLASSIFICATION

Botanical: *Albizia julibrissin* (Willd.) Durazz 'SUMMER CHOCOLATE'.

Parentage: Seedling selection of the variety *Albizia julibrissin.*

Propagation: By bud grafting; scion growth is observed within 4 to 6 weeks of grafting.

PLANT

Size: Approximately 10 m tall and 10 m wide at maturity.

Habit: Upright, vase-shaped tree with domed crown.

Foliage: Alternate, bipinnately compound with 40 to 60 leaflets.

Shape: Oblong-falcate.

*Leaf apex*.—Occasionally acute to elliptic.

*Leaf base*.—Rounded to obtuse.

*Leaf size*.—Approximately 30 cm long and 18 to 20 cm wide; leaflets approximately 0.5 to 1 cm long.

Color:

*New growth*.—New leaves emerge green. Upper Side: Near Grey-Green Group 189A. Underside: Near Grey-Green Group 189A.

*Mature foliage color*.—Upper Side: Near Grey-Purple Group 187A. Underside: Near Grey-Purple Group 187A.

*Petiole color*.—Near Greyed-Purple Group 185C.

*Rachilla color*.—Near Greyed-Purple Group 185C.

*Stipules*.—None noted.

*Margins*.—Entire.

*Texture*.—Underside: Ciliate to pubescent on the mid-rib.

Trunk diameter: Approximately 1 cm at 3 m above soil level.

Bark:

*Texture*.—Glabrous.

*Color*.—Near Greyed-Green Group 198C.; lenticles near White Group 155B.

Branches:

*Diameter*.—Typical branch approximately 5 mm in diameter.

*Texture*.—Glabrous.

*Color*.—Near Grey-Brown Group 199A.

Hardiness: USDA Zone 7 (0° F. to 10° F.).

Vigor: From initial graft to 8 feet in height in 1 growing season (9 months).

Pests/diseases: No resistance or susceptibility to pests or disease problems beyond that of the species has been noted.

INFLORESCENCE

Bloom period: Summer.

Inflorescence type: A many-flowered head; the heads are arranged in a corymb.

Flower form: Each flower consists of a 5-petaled calyx and corolla fused into a tube with numerous stamens and a central pistil; the central flower in each head is much larger that the other flowers in the head.

Flower head size: Approximately 3.5 cm in diameter.

Flower size (excluding stamen): Approximately 7 to 9 mm long.

Color:

*Floral tube*.—Near Yellow-Green Group 151B.

*Stamen base*.—Near White Group 155D.

*Stamen tips*.—Near Red-Purple Group 62A to 62C.

Peduncle:

*Length*.—7 mm.

*Width*.—Less than 1 mm.

*Color*.—Near Greyed-Purple Group 185D.

Color: Burgundy.

Fragrance: None noted.

REPRODUCTIVE ORGANS

Stamens:

*Number*.—Variable, from 15 to 20.

*Length*.—7–9 mm long.

Pistil: Same length or slightly longer than stamens.

Fruit:

*Type*.—Thin, flat legume.

*Size*.—18 to 20 cm long.

*Color*.—Near Grey-Purple Group 187A.

I claim:

1. A new and distinct tree variety of *Albizia julibrissin* of the variety substantially as shown and described.

* * * * *